|   | United States Patent [19] | [11] | 4,370,348 |
|---|---|---|---|
|   | Shriver | [45] | Jan. 25, 1983 |

[54] METHOD OF INDUCING CYTOPROTECTION

[75] Inventor: David A. Shriver, Martinsville, N.J.

[73] Assignee: Ortho Pharmaceutical Corporation, Raritan, N.J.

[21] Appl. No.: 270,165

[22] Filed: Jun. 3, 1981

[51] Int. Cl.³ ............................................ A61K 31/12
[52] U.S. Cl. .................................................... 424/331
[58] Field of Search ........................................ 424/331

[56] References Cited

U.S. PATENT DOCUMENTS 4,132,783  1/1979  Kluender et al. ................... 424/331

Primary Examiner—Sam Rosen
Attorney, Agent, or Firm—Benjamin F. Lambert

[57] ABSTRACT

A method of inducing cytoprotection in mammals utilizing the prostaglandin derivative 16-methyl-1,11α,16RS-trihydroxyprost-13E-en-9-one is described.

8 Claims, No Drawings

METHOD OF INDUCING CYTOPROTECTION

Prostaglandins (PG) are a family of 20 carbon oxygenated fatty acids which are biochemically derived from arachidonic acid. There are approximately twenty naturally occurring prostaglandins and numerous analogs have been synthetized. To date, no other antacoids, substances which are formed by cells of one organ and carried through the circulation to act upon the cells of other organs, have more numerous or diverse effects than do prostaglandins.

In the gastrointestinal tract, the reduction of the acid burden of the gastrointestinal tract has long been recognized, as a viable therapeutic approach for the management of peptic ulcer disease. Prostaglandin $E_1$ ($PGE_1$), $PGE_2$ and several PGE analogs have been shown to have gastric antisecretory activity in both laboratory animals and man. However, the clinical usefulness of these compounds as gastric antisecretory agents has been limited by the appearance of gastrointestinal side effects, namely nausea, vomiting, intestinal colic and diarrhea.

There is, however, another action of some prostaglandins on the gastrointestinal tract which appears to be unrelated to their ability to inhibit acid secretion. This action is called "cytoprotection". The word is used to describe the ability of some prostaglandins to increase the natural integrity of the gastrointestinal mucosa. The cytoprotective activity of a compound can be observed in both animals and man by noting the increased resistance of the gastrointestinal mucosa to the noxious effect of strong irritants, e.g., the ulcerogenic effects of aspirin or indomethacin. In addition to lessening the effect of nonsteroidal anti-inflammatory drugs on the gastrointestinal tract, animal studies show that cytoprotective prostaglandins will prevent gastric lesions induced by oral administration of strong acids, strong bases, ethanol, hypertonic saline solutions, and even boiling water. The cytoprotective activity of prostaglandins does not appear to be related to their ability to inhibit gastric acid secretion because:

(a) The cytoprotective dose is a small fraction of the antisecretory dose, in the case of prostaglandins that exhibit antisecretory activity. In many cases, the antisecretory $ED_{50}$ is more than 100 times higher than the cytoprotective dose.

(b) Certain cytoprotective prostaglandins are not antisecretory at any dose when given orally to rats [e.g., 16,16-dimethyl $PGA_2$, 15(R)-15-methyl $PGF_2\beta$].

(c) Other antisecretory agents such as cimetidine and methscopolamine bromide, as well as antacids, are not cytoprotective in the models employed (Gastroenterology, 77: 433–443, 1979).

In addition, cytoprotective activity does not appear to be a property of all prostaglandins since oral administration of either $PGA_1$ or $PGD_2$ does not protect rats from indomethacin-induced gastric lesions (Advances in Prostaglandin and Thromboxane Research, Vol. 2, ed. B. Samuelsson and R. Paoletti., Raven Press, New York, N.Y., 1976 pp. 507–520).

There is no apparent structure-activity relationship for compounds exhibiting cytoprotective activity. Cytoprotective prostaglandins have no common structural configuration, therefore, it is not possible to predict which prostaglandins or PG analogs will exhibit cytoprotective activity and which will not. For example, $PGE_2$ does not exhibit antisecretory activity in humans but is cytoprotective in humans, while in animals two prostaglandins, $PGA_1$ and $PGD_2$, exhibit antisecretory activity but are not cytoprotective.

16-Methyl-1, 11α, 16RS-trihydroxyprost-13E-en-9-one (ORF-15927) is a known prostaglandin analog which is described in U.S. Pat. No. 4,132,738 and has the following structural formula:

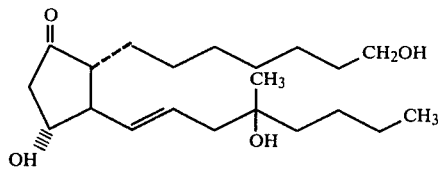

The compound is a reduction product of a prostaglandin of the E ($PGE_1$) class and is a known orally effective gastric antisecretory agent. It has now been discovered that this compound prevents gastric lesions induced by a variety of irritating substances, including acetylsalicylic acid, ethanol, strong acids, strong bases, hypertonic saline and boiling water. These effects are cytoprotective because they occur at doses lower than those doses which inhibit acid secretion. Increasing the resistance of the gastrointestinal mucosa will find therapeutic utility in diseases where the integrity of the gastrointestinal mucosa is compromised, such as in peptic ulcer disease and inflammatory bowel disease. For example, in peptic ulcer disease, 16-methyl-1,11α,16RS-trihydroxyprost-13E-en-2-one, at the proper dosages, will promote healing of an existing ulcer and prevent reoccurrence of future ulcers.

The prostaglandin analog of this invention has been found to exhibit cytoprotective properties at doses between 2–200 micrograms. The preferred dose is between 20–40 micrograms. The compound can be administered orally, subcutaneously or intravenously. However, the preferred route of administration is oral.

In practical use, the compound can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

The $PGE_1$ analog is prepared according to the method described in U.S. Pat. No. 4,132,738.

EVALUATION OF CYTOPROTECTIVE EFFECTS

Rat Cytoprotection

Male Charles River CD rats weighing between 140 and 200 g. were fasted overnight with water ad lib. The rats were pretreated orally with the compound or glycol vehicle* in a dosage volume of 1.0 ml/kg. One hour later the necrotizing agent acetylsalicylic acid (ASA) at 40 and 80 mg/kg suspended in 0.5% methylcellulose (1500 cps.) or 37.5% ethanol were administered orally in a dose volume of 1 ml/kg body weight or 1 ml/rat, respectively. Rats were killed with $CO_2$ one hour later, the stomachs removed, inflated with water, and opened along the greater curvature. The presence of mucosal bleeding was noted and the mucosa was wiped off. The incidence of lesions in the submucosa was observed and scored on the following arbitrary severity scale:

0 = normal
1 = submucosal redness
2 = number of submucosal lesions less than 3 mm in any dimension
3 = number of submucosal lesions greater than 3 mm in any dimension

*Polyethylene glycol 200—60% Polyethylene glycol 400—20% Ethanol 200 proof—20%

The incidence of mucosal and submucosal lesions was statistically compared to the pooled control group by the method of Chi-squares using Yates correction (Goldstein, A.; *Biostatistics: An Introductory Text,* MacMillan Co., N.Y., 1967), while the sum of the Products of the severity scores times the number of lesions with that particular score were calculated for each animal and compared by Student's t-test to the pooled control group using the pooled error variance to make t-comparisons (Steel, R. G. D. and Torrie, J. H., *Principles and Procedures of Statistics,* McGraw-Hill Co., Inc., New York, N.Y., 1960).

Rat Cytoprotection

The results of the cytoprotective studies using the necrotizing agent ASA (Table 1) shows that ORF-15927 protected the gastric mucosa and submucosa from ulceration. The compound also protects rat gastric mucosa and submucosa from ethanol-induced lesions (Table 2).

The lowest statistically significant cytoprotective dose of the compound for ASA-induced lesions and ethanol-induced lesions was 15 μg/kg. At this dose, the compound reduced the incidence of gastric mucosal and submucosal lesions in the 40 mg/kg aspirin and ethanol groups while only the submucosal lesions were reduced following the 80 mg/kg aspirin treatment. As might be expected, the higher dose of aspirin was more resistant to the cytoprotective effects of the compound. Also, in all cases where there were gastric lesions, the Severity Score is greater for the 80 mg/kg aspirin group than for the 40 mg/kg aspirin group, and the first indication of activity was observed in the Severity Score. The Severity Scores of the ethanol treated groups were less than that for aspirin treatments, which substantiates the observation that the macroscopic appearances of the two lesions were different.

The above results demonstrate that 16-Methyl-1,11α,16RS-trihydroxyprost-13E-en-9-one protects the gastric mucosa from lesions induced by aspirin and ethanol and that these protective doses are much lower than those required to inhibit gastric acid secretion. Table 3 shows the minimum effective antisecretory dose of ORF-15927 to be 2000 μg/kg by the intraduodenal route. This dose is approximately 133 times the minimum effective cytoprotective doses shown in Tables 1 and 2. These newly discovered cytoprotective properties therefore appear at doses which are not effective for antisecretory purposes.

TABLE 1

CYTOPROTECTION OF ORALLY ADMINISTERED PROSTAGLANDIN IN ACETYLSALICYLIC ACID TREATED RATS

| Treatment | Dose[a] (μg/kg) | Ulcer Incidence 40 mg/kg, ASA Mucosa | 40 mg/kg, ASA Submucosa | 80 mg/kg, ASA Mucosa | 80 mg/kg, ASA Submucosa | Severity Score 40 mg/kg, ASA | Severity Score 80 mg/kg, ASA |
|---|---|---|---|---|---|---|---|
| Pooled Control | | 109/135 | 102/135 | 57/69 | 54/69 | 12.5 | 13.7 |
| ORF-15927 | 0.15 | 7/10 | 7/10 | —[c] | — | 8.3 | — |
| | 0.75 | 10/10 | 9/10 | — | — | 22.1 | — |
| | 1.5[b] | 23/30 | 23/30 | 8/10 | 7/10 | 9.4 | 10. |
| | 15.0[b] | 5/27* | 5/27* | 6/10 | 4/10* | 1.2 | 2.1 |
| | 31.25 | 2/30* | 1/30* | 8/20* | 1/20* | 0.3 | 1.8 |
| | 62.5 | 0/10* | 0/10* | 1/10* | 1/10* | 0.0 | 0.6 |
| | 150.0 | 4/10* | 3/10* | — | — | 3.9 | — |
| | 250.0 | 0/8* | 0/8* | 0/9* | 0/9* | 0.0 | 0.0 |
| | 300.0 | 0/10* | 0/10* | — | — | 0.0 | 0.0 |

*$p \leq 0.05$ when compared to individual control group
[a]Prostaglandins were given 1 hour before ASA and the stomachs were evaluated 1 hr. after ASA administration
[b]Data from doses of $1.56 \times 10^{-6}$ and $1.56 \times 10^{-5}$ were combined with data from doses of $1.5 \times 10^{-6}$ and $1.5 \times 10^{-5}$, respectively.
[c]Not tested

TABLE 2

CYTOPROTECTIVE ACTIVITY OF THE PG1 ANALOG IN 37.5% ETHANOL TREATED RATS

| Treatment[a] | Dose (μg/kg) | Ulcer Incidence Mucosa | Submucosa | Severity Score |
|---|---|---|---|---|
| Vehicle | 0 | 44/49 | 38/49 | 7.3 |
| ORF-15927 | 1.5 | 10/10 | 10/00 | 11.3 |
| | 15.0 | 5/10* | 3/10* | 3.3 |
| | 62.5 | 0/8* | 0/8* | 0.0 |
| | 125.0 | 0/9* | 0/9* | 0.0 |
| | 250.0 | 0/10* | 0/10* | 0.0 |
| | 500.0 | 0/10* | 0/10* | 0.0 |
| | 1000.0 | 0/20* | 0/20* | 0.0 |

*$p \leq 0.05$
[a]ORF-15927 was given 1 hr. before EtOH and the stomachs were evaluated 1 hr after EtOH administration.

TABLE 3
THE GASTRIC ANTISECRETORY ACTIVITY ($\bar{x} \pm$ S.E.)
OF INTRADUODENALLY ADMINISTERED ORF-15297 IN THE FOUR HOUR
PYLORUS LIGATED RAT[b]

| Treatment | Dose (μg/kg) | N | Volume (ml) | Hydrogen in Conc. (meq/ml) | Total Hydrogen Ion Secreted (meq) |
|---|---|---|---|---|---|
| Buffered Glycol Vehicle | | 9 | 5.6 ± 0.5 | 1.13 ± 0.03 | 0.64 ± 0.07 |
| ORF-15927 | 500 | 8 | 6.0 ± 0.6 | 1.12 ± 0.07 | 0.70 ± 0.09 |
| | 2000 | 10 | 3.8* ± 0.5 | 0.97* ± 0.04 | 0.37* ± 0.05 |
| | 8000 | 10[a] | 1.7* ± 0.2 | 0.74* ± 0.04 | 0.14* ± 0.01 |

*$p \leq 0.05$ compared to vehicle controls
[a]2/10 rats had volumes of gastric juice too small to measure.
[b]Method carried out according to procedure disclosed in Shay et al., Gastroenterology, 26:906, 1954

Preparation of
16-methyl-1,11α,16RS-trihydroxyprost-13E-en-9-one

A. Preparation of Iodovinylalcohol

[1-Iodo-4-methyloct-1E-en-4RS-ol]

A 12.2 g portion of magnesium turnings was heat dried under argon in a 500 ml. flask fitted with an air stirrer, condensor and addition funnel. After cooling the flask, 60 ml of dry ether was added, followed by a small portion of a solution of 33.9 ml of propargyl bromide in 60 ml of dry ether followed by 50 mg of mercuric chloride. After spontaneous ether reflux indicated that the reaction had commenced, the remainder of the propargyl bromide solution was added dropwise to the mixture to maintain gentle reflux. After the addition was complete, the reaction mixture was stirred for an additional one-half hour. A solution of 25 g of 2-hexanone, commercially available, in 25 ml of dry ether was then added to the reaction mixture, again at a rate to maintain gentle reflux. A heated oil bath was then used to reflux the final mixture for another hour. The final mixture was then quenched by the addition of water, followed by 10 percent hydrochloric acid to dissolve solid salts. The phases were separated and the ether extract was washed with brine and saturated sodium bicarbonate solution. It was then dried over MgSO$_4$ and then distilled using a water pump to successively remove ether and a trace of 2-hexanone (bp ca 30°). A 22.4 g portion (64 percent) of the acetylenic alcohol intermediate, methyloct-1-yn-4RS-ol, bp 70°-76° (ca 20 mm) was recovered. Glc analysis of this product showed a 20 percent impurity thought to be 4-methylocta-1,2-dien-4RS-ol. The distilled 80 percent pure alcohol was used in successive experiments. The material had the following spectral characteristics: nmr (CDCl$_3$)δ 0.93 (3H, broad t, J=5 Hz), 1.0 to 1.7 (6H,m), 1.28 (3H,S), 1.82 (1H,s), 2.12 (1H, t, J=3 Hz) and 2.39 ppm (2H, d, J=3 Hz); ir (CHCl$_3$) 1120, 1380, 1460, 2120, (weak), 2870, 2930, 2960, 3300, 3200 to 3600 broad and 3590 cm$^{-1}$.

The 4-methyloct-1-yn-4RS-ol was converted to the corresponding iodovinylalcohol, 1-Iodo-4-methyloct-1E-en-4RS-ol as described below.

A solution of 30 ml (169 mmol) of diisobutylaluminum hydride in 75 ml of dry toluene was stirred under argon with ice water bath cooling as a second solution of 7.0 g (50 mmol of the 4-methyloct-1-yn-4RS-ol, in 25 ml of dry tuolene was added dropwise over a period of one hour. Stirring was then continued without cooling for one hour and then with oil bath warming (50°-60° C.) for three hours. The oil bath was then replaced with a dry ice-acetone (−78° C.) bath as a third solution of 42.8 g (169 mmol) of iodine in dry tetrahydrofuran to total 100 ml was added dropwise to the reaction mixture maintaining a stirring of the reaction mixture. The cooling bath was then removed and the reaction mixture was allowed to come to 20° slowly before it quenched by being forced under a slight argon pressure through polyethylene tubing into a vigorously stirred mixture of ether and two percent aqueous sulfuric acid. The ether phase was removed and then washed successively with another portion of two percent sulfuric acid, brine, saturated aqueous sodium bicarbonate and brine. It was dried over Na$_2$SO$_4$ and evaporated under reduced pressure. The residue (10.3 g) was chromatographed on silica gel to yield 1.4 g of partially pure and 1.2 g of pure 1-Iodo-4-methyloct-1E-en-4RS ol, along with several grams of highly contaminated material. The impure fractions were each distilled at 0.1 mm to yield a total of 2.35 g of recovered acetylenic alcohol (bp 50°-55° C.) and 2.55 g of reasonably pure iodovinyl-alcohol (bp 60°-65° C.). The total yield of pure iodovinylalcohol was thus 3.8 g: nmr (CDCl$_3$)δ 0.93 (3H, broad t, J=5 Hz), 1.18 (3H,s), 1.0-1.7 (6H,m), 2.20 (1H,s), 2.25 (2H, d, J=7 Hz), 6.20 (1H, d, J=15 Hz) and 6.73 ppm (1H, d of t, J=15, 7 Hz); ir (film) 750, 900, 940, 1140, 1380, 1465, 2870, 2930, 2960, and 3200-3600 cm$^{-1}$ (broad).

The conversion of the acetylenic alcohol can be carried out by replacing diisobutylaluminum hydride with disiamylborane; a base, for example an alkali metal hydroxide such as sodium or potassium hydroxide; a trialkylamine oxide such as trimethylamine oxide; and iodine.

B. Preparation of Organolithiocuprate from Iodovinylalcohol (1) Preparation of
1-Iodo-4-methyl-4RS-(tetrahydropyranyloxy) oct-1E-ene The hydroxyl function of the iodovinylalcohol prepared as described above was protected as described below.

A solution of 0.806 g (3.00 mmol) of 1-iodo-4-methyloct-1E-en-4RS-ol, 0.34 ml (3.73 mmol) of dihydropyran and a 5 mg portion of toluenesulfonic acid in 1.5 ml of dry ether was stirred in a flask under argon. Tlc (CHCl$_3$, silica gel) analysis after one and one-half hours indicated that the reaction was not completed; an additional 0.2 ml portion of dihydropyran and about 5 mg of toluenesulfonic acid were added, followed after another hour with another 0.5 ml portion of dihydropyran and toluenesulfonic acid. After a period of one and one-half hours, solid potassium carbonate was added to the reaction mixture. After stirring for several minutes the resultant mixture was washed with water. The washed solution was back extracted with ether three times. The combined extract was dried (Na$_2$SO$_4$) and evaporated in vacuo to yield 1.16 g of the title compound: nmr (CDCl$_3$)δ 0.95 (3H,m), 1.20 (3H,s) 1.0-1.8

(12H,m) 2.3 (2H,d, J=8 Hz), 3.3–4.2 (2H,m) 4.82 (1H broad s), 6.12 (1H, d, J=14 Hz) and 6.73 ppm (1H,d of t, J=14, 7 Hz); ir (CHCl₃) 870, 950, 990, 1020, 1070, 1125, 1380, 1470, 1610, 2870 and 2930 cm⁻¹.

(2) Preparation of Organolithiocuprate from Protected Iodovinylalcohol

A solution of 1.06 g (3.00 mmol) of 1-iodo-4-methyl-4RS (tetrahydropyranyloxy)-oct-1E-ene, in 10 ml of dry ether was stirred in a flask under argon with −78° bath cooling as 5.5 ml (6.00 mmol of a 1.18 M solution of t-butyllithium in pentane was added dropwise via syringe. The resultant solution was stirred at −78° for two hours.

A second solution was prepared by stirring under argon a suspension of 9.392 g (3.00 mmol) of dry copper (I) pentyne in 5 ml of dry ether solubilized with 1.10 ml of hexamethylphosphorous triamide, until it became homogeneous. This second solution was then transferred via syringe to the above alkenyllithium reaction mixture as it was stirred with −78° bath cooling. The desired lithiocuprate reagent, an orange mixture, was stirred 15 minutes after addition was complete.

C. Substituted 2-Cyclopenten-1-one 4R-(tetrahydropyran-2-yloxy)-2[7-tetrahydropyran-2-yloxy)heptyl]-2-cyclopenten-1-one was prepared from the appropriate 2-(w-hydroxyalkyl)-cyclopenten-1,3,4-trione as described in *Tetrahedron Letters*, 2063 (1977) and described in detail hereinbefore.

D. Prostaglandin Synthesis

The synthesis of the prostaglandin E₁ analog was achieved as described below.

A solution of 0.783 g (2.06 mmol) of 4R-(tetrahydropyran-2-yloxy)-2[7-(tetrahydropyran-2-yloxy)heptyl]-cyclopent-2-enone, in 3 ml of dry ether was added dropwise to the lithiocuprate reaction mixture as stirring was continued at −78°. After addition was complete, the resultant orange mixture was stirred for 10 min. at −78° and then at −20° for three hours.

The reaction was quenched at −20° by the addition of sufficient two percent aqueous sulfuric acid to give an acidic aqueous phase after stirring. The resultant mixture was thoroughly shaken and then filtered through Celite. The filter pad was rinsed thoroughly with ether. The filtrate phases were separated and the organic phase was washed with brine and saturated aqueous sodium bicarbonate. It was then dried over MgSO₄ and evaporated in vacuo to yield 1.5 g of residue containing the tetrahydropyran-protected form of the analog.

This residue was dissolved in 20 ml of acetic acid-water-tetrahydrofuran (65:35:10) and left to stand under argon for 41.5 hours at room temperature and the resultant solution evaporated in vacuo to remove the solvent. The residue was dissolved in ethyl acetate and washed with saturated aqueous sodium bicarbonate. The wash solution was back extracted with ethyl acetate. The combined extract was dried over MgSO₄ and evaporated in vacuo to yield 1.29 g of a yellow residue. This residue was chromatographed on silicic acid-diatomaceous earth (85:15) using benzene-ethyl acetate gradient elution to yield 193.1 mg (26.5 percent) of the pure PGE₁ analog along with less polar materials that appeared to contain the PGE₁ analog, and as a side-product, the PGA analog, both protected as tetrahydropyran-2-yl-ethers. These less polar materials were dissolved in another portion of acetic acid-water-tetrahydrofuran and left under argon for three days. The product was isolated as earlier described. The spectral characteristics of the analog and the side product PGA were:

ORF 15927 [α]$_D$−58.6° (c 1.0, CHCl₃); R$_f$(system II) 0.29; nmr (CDCl₃)δ 0.93 (3H,m), 1.17 (3H,s), 1.0–2.7 (24H,m) 3.63 (5H, broad s over broad t, J=6.0 Hz), 4.20 (1H, q, J=7.0 Hz) and 5.64 ppm (2H,m); ir (CHCl₃) 895, 970, 1065, 1150, 1740, 2860, 2930 and 3200–3600 cm⁻¹; ms (70 eV) 336 (p-H₂O), 318 (p-2H₂O), 278, 264, 253, 235, 217, 193.

As indicated above, cytoprotection by the PGE₁ analog is unrelated to the inhibition of gastric acid secretion since (1) it is maximal at doses that have no effect on gastric secretion and (2) antisecretory compounds and antacids generally are not cytoprotective. Although the mechanism of gastric cytoprotection is unknown, it appears that the prostaglandin increases the resistance of gastric mucosal cells to the necrotizing effect of strong irritants. It is suggested, therefore, that the PGE₁ analog, by a mechanism other than the inhibition of gastric acid secretion, maintains the cellular integrity of the gastric mucosa and might be beneficial in the treatment of a variety of diseases in which injury to the gastric mucosa is present.

What is claimed is:

1. The method of inducing cytoprotection in mammals by increasing the natural integrity of the gastrointestinal mucosa which comprises administering to a mammal in need of such therapy a cytoprotective-effective amount of a prostaglandin derivative of the formula

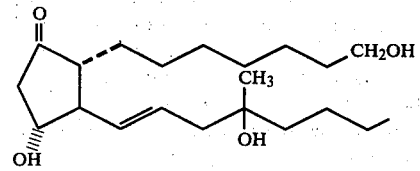

in a pharmaceutically acceptable carrier.

2. The method of claim 1 wherein the prostaglandin is administered orally.

3. The method of claim 1 wherein the prostaglandin is administered in daily unit dosage form.

4. The method of claim 1 wherein the prostaglandin derivative is administered at a dosage level between 2–200 micrograms.

5. The method of preventing gastrointestinal lesions in mammals which comprises administering to said mammal in need of such therapy a cytoprotective-effective amount of the prostaglandin derivative 16-methyl-1,11α,16RS-trihydroxyprost-13E-en-9-one in a pharmaceutically acceptable carrier.

6. The method of claim 5 wherein the prostaglandin derivative is administered at a dosage level between 2–200 micrograms.

7. The method for treating gastrointestinal lesions in mammals which comprises administering to said mammal in need of such therapy a cytoprotective-effective amount of the prostaglandin derivative 16-methyl-1,11α,16RS-trihydroxyprost-13E-en-9-one in a pharmaceutically acceptable carrier.

8. The method of claim 7 wherein the prostaglandin derivative is administered at a dosage level between 2–200 micrograms.

* * * * *

UNITED STATES PATENT OFFICE
CERTIFICATE OF CORRECTION

Patent No. 4,370,348    Dated January 25, 1983

Inventor(s) David A. Shriver

It is certified that error appears in the above-identified patent and that said Letters Patent are hereby corrected as shown below:

Column 8, line 35

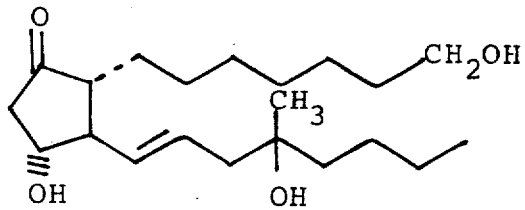

should be

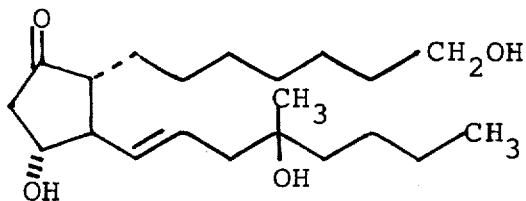

Signed and Sealed this

Twenty-ninth Day of April 1986

[SEAL]

Attest:

DONALD J. QUIGG

Attesting Officer    Commissioner of Patents and Trademarks